(12) United States Patent
Cheng et al.

(10) Patent No.: US 8,048,542 B2
(45) Date of Patent: Nov. 1, 2011

(54) BIS-PHENANTHROIMIDAZOLYL COMPOUND AND ELECTROLUMINESCENT DEVICE USING THE SAME

(75) Inventors: Chien-Hong Cheng, Hsinchu (TW); Charng-Hsing Liu, Tainan County (TW); Fang-Iy Wu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 334 days.

(21) Appl. No.: 12/417,371

(22) Filed: Apr. 2, 2009

(65) Prior Publication Data
US 2010/0253208 A1 Oct. 7, 2010

(51) Int. Cl.
*H01J 1/63* (2006.01)
*C07D 403/02* (2006.01)

(52) U.S. Cl. ........ 428/690; 428/917; 313/504; 313/506; 548/301.7

(58) Field of Classification Search ........................ None
See application file for complete search history.

(56) References Cited

U.S. PATENT DOCUMENTS
5,281,489 A * 1/1994 Mori et al. .................... 428/690

FOREIGN PATENT DOCUMENTS
WO WO 2004/030029 * 4/2004

OTHER PUBLICATIONS

Kuo et al., Journal of Materials Chemistry, (2009), vol. 19, pp. 1865-1871.*
Xie et al., Journal of Materials Chemistry, (2007), vol. 17, pp. 861-865.*
Song et al., Tetrahedron Letters, vol. 48, (2007), pp. 5397-5400.*

* cited by examiner

*Primary Examiner* — Dawn L. Garrett
(74) *Attorney, Agent, or Firm* — Muncy, Geissler, Olds & Lowe, PLLC

(57) ABSTRACT

A bis-phenanthroimidazolyl compound having a following formula is disclosed.

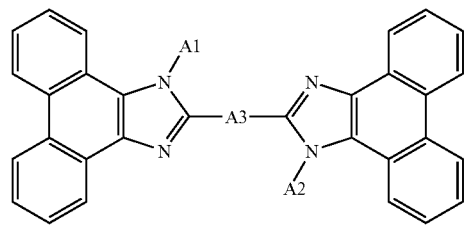

Where A1 and A2 comprise identical or different aromatic rings, A3 comprises a polyaromatic hydrocarbon or at least two aromatic groups, and each carbon in A1 to A3 and phenanthrol groups is independently substituted or non-substituted. The bis-phenanthroimidazolyl compound exhibits relatively better thermal properties with higher glass-transition temperature and efficient blue emission. The bis-phenanthroimidazolyl compound may function as a host emitter or charge-transporter. An electroluminescent device is also disclosed.

16 Claims, 7 Drawing Sheets

BIS-PHENANTHROIMIDAZOLYL COMPOUND AND ELECTROLUMINESCENT DEVICE USING THE SAME

BACKGROUND OF THE INVENTION

1. Field of the Invention

The present invention relates to a bis-phenanthroimidazolyl compound and an electroluminescent device using the same, particularly to a bis-phenanthroimidazolyl compound functioned as a host emitter or charge-transporter in an organic light emitting diode (OLED).

2. Description of the Prior Art

Organic light emitting diode (OLED) has been a great topic of interest for many researchers due to its advantageous application in flat panel displays. The development of stable and highly efficient three primary color (red, green and blue) emitting materials and devices is crucial for OLEDs to become commercial products. One important requirement in the development of organic electroluminescent devices is to develop RGB (red, green, and blue) light emitting devices so as to satisfy the need of a color flat panel display.

The hunt for efficient blue electroluminescence is of particular interest because it is an essential component to realize OLEDs in display as well as lighting applications. Many research groups have successfully prepared efficient blue fluorophores and their OLEDs. However, at the present time, the efficient ones with good Commission Internationale d'Énclairage y coordinate value ($CIE_y$) $\leq 0.15$ are still relatively rare. At the present time, there is a lack of good organic electroluminescence compounds that will satisfy the aforementioned need.

To sum up, it is highly desirable to develop new organic compounds that can be advantageously used in the low power consumption organic electroluminescent devices which can emit luminescence especially in blue color spectrum.

SUMMARY OF THE INVENTION

The present invention is directed to provide a bis-phenanthroimidazolyl compound and its application in an organic electronic device, especially in an organic light emitting diode (OLED), as a host emitter or charge-transporter.

According to an embodiment, a bis-phenanthroimidazolyl compound comprises the following formula.

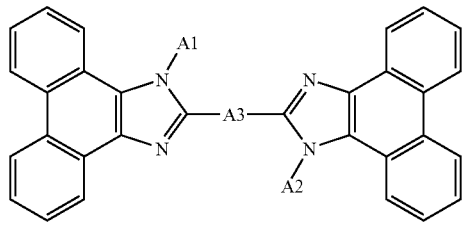

wherein A1 and A2 comprise identical or different aromatic rings, A3 is a member selected from the group consisted of naphthalene, anthracene, phenanthrene, chrysene, and pyrene, and each carbon in A1 to A3 and phenanthrol groups is independently substituted or non-substituted.

The present invention is also directed to provide an electroluminescent device giving relatively low turn-on voltages and pure-blue light with better color purity to realize higher power efficiency. Moreover, the efficiency may still retain at a high level even as the brightness level increased.

According to another embodiment, an electroluminescent device includes a cathode, an anode, and an organic layer provided in between the cathode and the anode. The organic layer comprises a compound comprising the following formula:

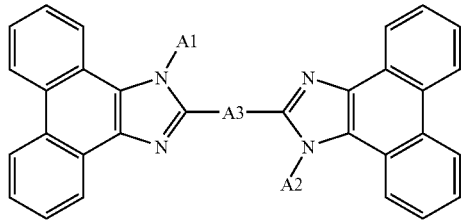

where A1 and A2 comprise identical or different aromatic rings, A3 comprises a polyaromatic hydrocarbon or at least two aromatic groups, and each carbon in A1 to A3 and phenanthrol groups is independently substituted or non-substituted.

Other advantages of the present invention will become apparent from the following description taken in conjunction with the accompanying drawings wherein are set forth, by way of illustration and example, certain embodiments of the present invention.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein.

DESCRIPTION OF THE PREFERRED EMBODIMENT

The present invention provides a novel bis-phenanthroimidazolyl compound which may be used in fabricating the light emitting layer and may also serve as the electron-transporting layer. The present invention also provide an electroluminescent (EL) device including the aforementioned bis-phenanthroimidazolyl compound, so as to provide improved luminescence, as well as simplify the construction of organic electroluminescent devices.

The bis-phenanthroimidazolyl compound for electron-transporting and electroluminescence comprising the following formula is provided.

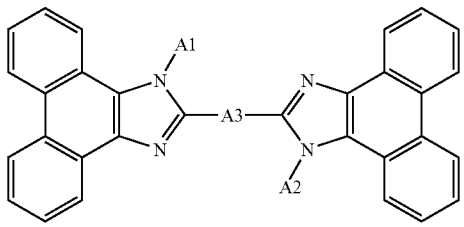

Wherein A1 and A2 comprise identical or different aromatic rings. A3 comprises a polyaromatic hydrocarbon or at least two aromatic groups. Each carbon in A1 to A3 and phenanthrol groups is independently substituted or non-substituted. A substituent group of carbons in A1 to A3 and phenanthrol groups may selectively comprise a halogen atom, a C1~C20 alkyl chain, a C1~C20 alkoxyl chain, a C1~C20 halogen substituted alkyl chain, a C1~C20 halogen substituted alkoxyl chain, a carbonyl group, a cyano group, or a nitro group.

In one preferred embodiment, the bis-phenanthroimidazolyl compound comprises two aromatic groups A4 and A5, and each carbon in A4 and A5 is independently substituted or non-substituted. A substituent group of carbons in A4 and A5 may selectively comprise a halogen atom, a C1~C20 alkyl chain, a C1~C20 alkoxyl chain, a C1~C20 halogen substituted alkyl chain, a C1~C20 halogen substituted alkoxyl chain, a carbonyl group, a cyano group, or a nitro group. The linkage between A4 and A5 may be ortho-, meta-, or para-.

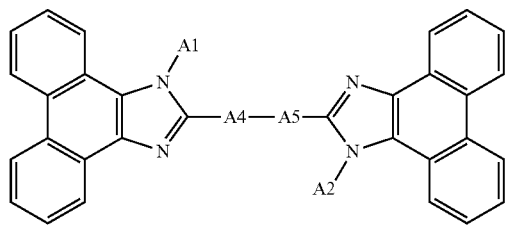

Another preferred example of the above-mentioned bis-phenanthroimidazolyl compounds is shown as follows.

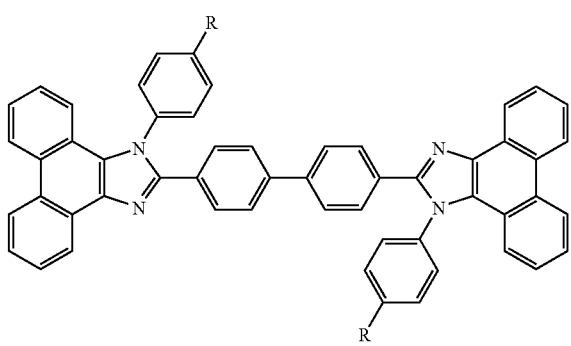

That is, A4 and A5 are phenyl groups, and A1 and A2 are selected from the group consisting of non, methyl-, and methoxyl-substituted phenyl ring.

Figure 1:
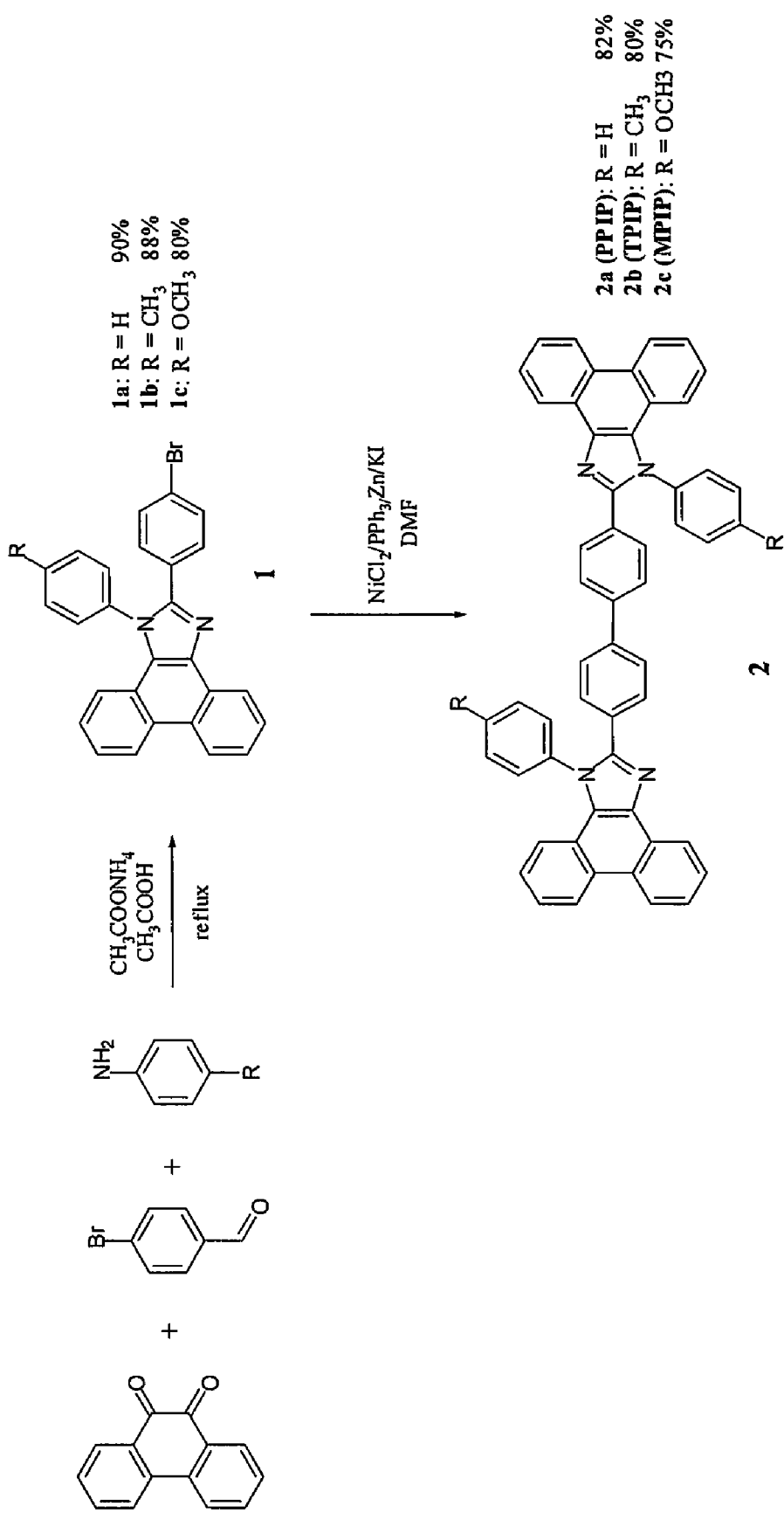
FIG. 1 is a schematic diagram illustrating synthesis of the bis-phenanthroimidazolyl derivatives according to an embodiment of the present invention.

The synthesis of the bis-phenanthroimidazolyl derivatives is illustrated in FIG. 1. Following are examples for 2-step preparation of bis-phenanthroimidazolyl compounds.

Synthesis of 2-(4-bromophenyl)-1-aryl-1H-phenanthro[9,10-d]imidazole derivatives 1a-1c 2-(4-Bromophenyl)-1-aryl-1H-phenanthro[9,10-d] imidazole derivatives (1a-1c) were prepared by refluxing 9,10-phenanthrenequinone (2.0 g, 9.6 mmol), 4-bromobenzaldehyde(1.78 g, 9.6 mmol), a substituted aniline (11.5 mmol) and ammonium acetate(7.4 g, 96.1 mmol) in glacial acetic acid (40 ml) for 24 hours under nitrogen atmosphere. After cooling to room temperature, the reaction mixture was then poured into a methanol solution with stirring. The separated solid was filtered off, washed with methanol and dried to obtain the expected product in good yields. The yields and important spectral data are given below.

2-(4-Bromophenyl)-1-phenyl-1H-phenanthro[9,10-d]imidazole derivatives (1a)

Yield: 3.88 g (90%). mp=255° C. $\delta_H$(200 MHz; CDCl$_3$; Me$_4$Si) 7.18 (td, J=8.0, J=1.1 Hz, 1H ), 7.25-7.30 (m, 1H), 7.39-7.56 (m, 7H), 7.58-7.78 (m, 5H), 8.70 (d, J=8.1 Hz, 1H), 8.76 (d, J=8.4 Hz, 1H), 8.84 (d, J=7.8 Hz, 1H); $\delta_C$(50 MHz; CDCl$_3$; Me$_4$Si) 120.8 (d), 122.7 (d), 122.9 (s), 123.1 (d), 123.4 (s), 124.1 (d), 125.0 (d), 125.7 (d), 126.3 (d), 127.1 (s), 127.3 (d), 128.3 (s), 129.0 (d), 129.4 (s), 129.5 (s), 130.0 (d), 130.3 (d), 130.8 (d), 131.4 (d), 137.5 (s), 138.6 (s), 149.7 (s). IR (KBr): 3055, 1594, 1494, 1450 cm$^{-1}$. HRMS (EI$^+$) Calc. for C$_{27}$H$_{17}$BrN$_2$: 448.0575, Found (M$^+$): 448.0576.

2-(4-Bromophenyl)-1-p-tolyl-1H-phenanthro[9,10-d]imidazole (1b)

Yield: 3.91 g (88%). mp=236° C. $\delta_H$(200 MHz; CDCl$_3$; Me$_4$Si) 2.53 (s, 3H), 7.17-7.27 (m, 2H), 7.30-7.53 (m, 9H), 7.58-7.67 (m, 1H), 7.73 (td, J=7.9, J=1.0 Hz, 1H), 8.68 (d, J=8.1 Hz, 1H), 8.74 (d, J=8.4 Hz, 1H), 8.83 (d, J=7.5 Hz, 1H); $\delta_C$(50 MHz; CDCl$_3$; Me$_4$Si) 21.5 (q), 120.8 (d), 122.6 (d), 122.9 (s), 123.1 (d), 123.2 (s), 124.0 (d), 124.9 (d), 125.6 (d), 126.2 (d), 127.1 (s), i27.3 (d), 128.2 (s), 128.3 (s), 128.60 (d), 129.3 (s), 129.5 (s), 130.7 (d), 130.9 (d), 131.4 (d), 135.8 (s), 137.3 (s), 140.1 (s), 149.7 (s). IR (KBr): 3047, 2966, 1609, 1513, 1450, 1373 cm$^{-1}$. HRMS (EI$^+$) Calc. for C$_{28}$H$_{19}$BrN$_2$: 462.0732, Found (M$^+$): 462.0729.

2-(4-Bromophenyl)-1-(4-methoxyphenyl)-1H-phenanthro[9,10-d]imidazole (1c)

Yield: 3.68 g (80%). mp=239° C. $\delta_H$(200 MHz; CDCl$_3$; Me$_4$Si) 3.95 (s, 3H), 7.09 (d, J=8.7 Hz, 2H), 7.22-7.34 (m, 1H), 7.39 (d, J=8.7 Hz, 2H), 7.44-7.56 (m, 6H), 7.61-7.68 (m, 1H), 7.74 (td, J=8.0, J=1.1 Hz, 1H), 8.70 (d, J=7.9 Hz, 1H), 8.76 (d, J=8.4 Hz, 1H), 8.83 (d, J=8.0 Hz, 1H); $\delta_C$(50 MHz; CDCl$_3$; Me$_4$Si) 55.6 (q), 115.3 (d), 120.8 (d), 122.6 (d), 123.0 (s), 123.1 (d), 123.3 (s), 124.1 (d), 125.0 (d), 125.6 (d), 126.3 (d), 127.1 (s), 127.3 (d), 128.2 (s), 128.4 (s), 129.3 (s), 129.5 (s), 130.1 (d), 130.8 (d), 130.9 (s), 131.4 (d), 137.3 (s), 149.9 (s), 160.4 (s). IR (KBr): 3055, 2959, 1609, 1513, 1450, 1251, 1030 cm$^{-1}$. HRMS (EI$^+$) Calc. for C$_{28}$H$_{19}$BrN$_2$O 478.0681, Found (M+): 478.0681.

Synthesis of Bis(phenanthroimidazolyl)biphenyl derivatives 2a-2c

To a round-bottom flask containing compound 1a (2.0 g, 4.45 mmol), NiCl$_2$(0.058 g, 0.45 mmol), Zn powder (0.29 g, 4.45 mmol), KI (1.11 g, 6.68 mmol), PPh$_3$ (0.47 g, 1.78 mmol) was purged with nitrogen three times, subsequently 20 mL of DMF was added to the flask and the mixture was stirred at 80° C. for 24 h under nitrogen. The Zn and inorganic salts were then removed by filtration of the hot reaction mixture and the residue also was washed with CH$_2$Cl$_2$. After evaporation of the filtrate under vacuum, the residue was collected and washed with methanol and then dried in vacuum to give product 2a(1.35 g, 82%). The product was further purified by vacuum sublimation technique at 330° C. and 3-5×10$^{-3}$ Pa. The other derivatives 2b and 2c were prepared according to a similar procedure from compounds 1b and 1c, respectively. The synthetic route to for bis-phenanthroimidazolyl derivatives is show in Scheme 1. The yields and important spectral data are given below.

4,4'-Bis(1-phenyl-1H-phenanthro[9,10-d]imidazole-2yl)-biphenyl (PPIP, 2a)

Yield: 1.35 g (82%). mp.=402° C. $\delta_H$(200 MHz; CDCl$_3$; Me$_4$Si) 6.73-7.79 (m, 28H), 8.72 (d, J=8.0 Hz, 2H), 8.79 (d, J=8.4 Hz, 2H), 8.89 (d, J=7.9 Hz, 2H). IR (KBr): 3055, 1595, 1494, 1451 cm$^{-1}$. HRMS (FAB$^+$) Calc. for C$_{54}$H$_{34}$N$_4$ 738.2783, Found (MH$^+$) 739.2861 Anal. Calc. for C$_{54}$H$_{34}$N$_4$: C, 87.78; H, 4.64; N, 7.58. Found: C, 87.67; H, 4.68; N, 7.52.

4,4'-Bis(1-p-tolyl-1H-phenanthro[9,10-d]imidazole-2yl)-biphenyl (TPIP, 2b)

Yield: 1.37 g (80%). mp.=405° C. $\delta_H$(200 MHz; CDCl$_3$; Me$_4$Si) 2.57 (s, 6H), 7.16-7.79 (m, 26H), 8.72 (d, J=8.0 Hz, 2H), 8.78 (d, J=8.4 Hz, 2H), 8.88 (d, J=7.9 Hz, 2H). IR (KBr): 3055, 2915, 1605, 1513, 1450, 1376 cm$^{-1}$. HRMS (FAB$^+$) Calc. for C$_{56}$H$_{38}$N$_4$: 766.3096, Found (MH$^+$) 767.3177. Anal. Calc. for C$_{56}$H$_{38}$N$_4$: C, 87.70; H, 4.99; N, 7.31. Found: C, 87.71; H, 5.01; N, 7.34.

4,4'-Bis(1-(4-methoxyphenyl)-1H-phenanthro[9,10-d]imidazole-2yl)-biphenyl (MPIP, 2c)

Yield: 1.34 g (75%). mp.=403° C. $\delta_H$(200 MHz; CDCl$_3$; Me$_4$Si) 3.98 (s, 6H), 6.73-7.79 (m, 26H), 8.72 (d, J=8.3 Hz, 2H), 8.78 (d, J=8.2 Hz, 2H), 8.88 (d, J=8.3 Hz, 2H). IR (KBr): 3062, 2959, 1601, 1509, 1458, 1249, 1031 cm$^{-1}$. HRMS (FAB$^+$) Calc. for C$_{56}$H$_{38}$N$_4$O$_2$: 798.2995, Found (MH$^+$) 799.3073. Anal. Calcd for C$_{56}$H$_{38}$N$_4$O$_2$: C, 84.19; H, 4.79; N, 7.01. Found: C, 84.18; H, 4.74; N, 7.03.

It is therefore understood by those skilled in the art that various compounds of the present invention may be formed by choosing different starting materials and different combinations of intermediates. For example, the 4-bromobenzaldehyde may be replaced with a substituted 4-bromobenzaldehyde; and the substituted aniline may be replaced with a 4-Aminopyridine.

It is also noted that bis-phenanthroimidazolyl derivatives were effectively synthesized from commercially available starting materials through simple two-step procedure in high yields without using expensive noble-metal catalysts. Moreover, the preparation procedure is suitable for large-scale production because no chromatographic purification is needed in the syntheses.

As illustrated in Table 1, these compounds exhibit relatively better thermal properties with higher glass-transition temperature of 197~200° C. and emits intense blue light in solution with emission peaks at 462~466 nm.

TABLE 1

Physical properties of the bis-phenanthroimidazolyl compounds 2

| Compound | T$_m$/T$_g$/T$_c$$^a$ (° C.) | $\lambda_{max}$ (abs)$^b$ (nm) | $\lambda_{em}$$^b$ (nm) | Quantum yield$^c$ (%) |
|---|---|---|---|---|
| 2a (PPIP) | 402/197/257 | 367 | 428, 445 | 58 |
| 2b (TPIP) | 405/200/232 | 368 | 429, 446 | 54 |
| 2c (MPIP) | 403/ND/ND | 368 | 429, 446 | 48 |

$^a$Obtained from DSC measurement;
ND: not detected.
$^b$Measured in dilute CH$_2$Cl$_2$ solution (<10$^{-5}$M).
$^c$Measured in dilute CH$_2$Cl$_2$ solution by using 2-aminopyridine as a reference (<10$^{-5}$M).

Figure 2:
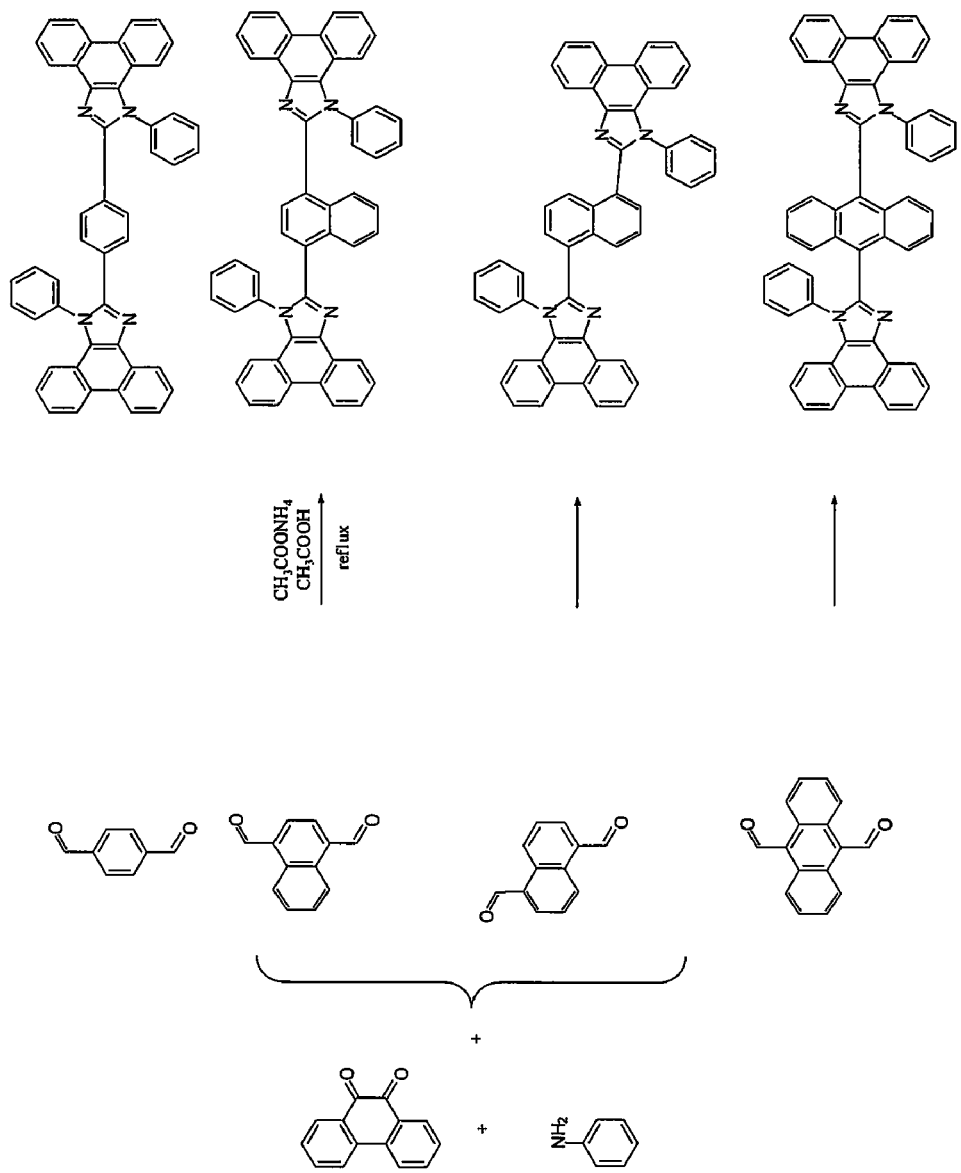
FIG. 2 is a schematic diagram illustrating synthesis of the bis-phenanthroimidazolyl derivatives according to an embodiment of the present invention.

As fore-mentioned, A3 may be a polyaromatic hydrocarbon; therefore, A3 may be a member selected from the group consisted of naphthalene, anthracene, phenanthrene, chrysene, and pyrene in one embodiment. FIG. 2 is a schematic diagram illustrating synthesis of the bis-phenanthroimidazolyl derivatives in which the A3 is naphthalene or anthracene.

As aforementioned, the novel bis-phenanthroimidazolyl compound may be used in preparing the light emitting layer and/or may serve as the electron-transporting layer. Therefore, an electroluminescent device according to one embodiment of the present invention includes a cathode, an anode, and an organic layer provided in between the cathode and the anode, wherein the organic layer comprises the aforementioned bis-phenanthroimidazolyl compounds. The organic layer may serve as a light emitting layer and/or an electron-transporting layer to establish the aforementioned electroluminescent device.

The electroluminescent device may further include a hole-transporting layer and/or an electron-transporting layer. The hole-transporting layer may include a 4,4'-bis[N-(1-naphthyl)-N-phenylamino]biphenyl (NPB), N,N'-di-m-tolyl-N,N-diphenyl-1,1'-biphenyl-4,4'-diamine (TPD), or 4,4',4"-tris(N-carbazolyl)triphenyl amine (TCTA). The electron-transporting layer may include a metal chelate, 1,3,4-oxadiazole or 1,2,4-triazole or a derivative thereof, a thiopyran sulfone or a derivative thereof, or bis(benzimidazolyl)perylenedicarboximide.

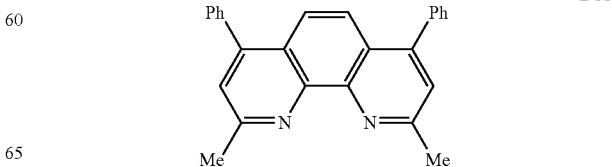

BCP

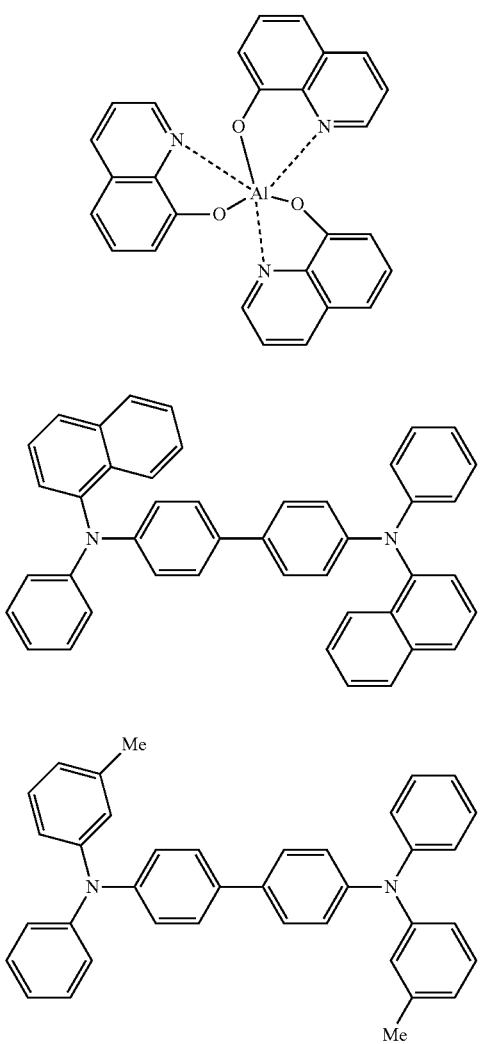

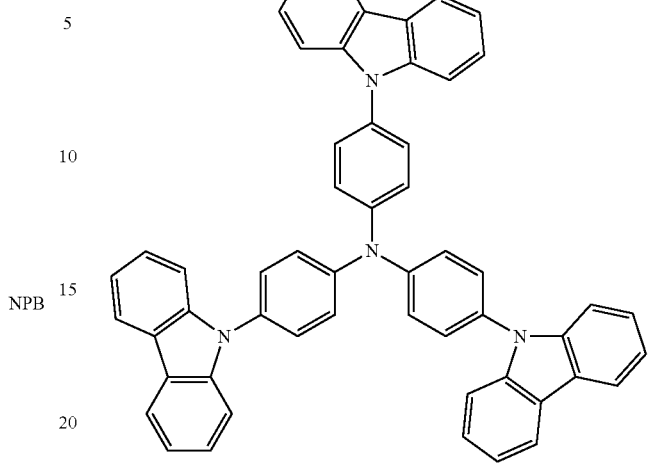

The electroluminescent device may also include an emitting layer. The emitting layer may include a host emitter, e.g. 9,10-Di(naphth-2-yl)anthracene (ADN), 1-(4-(1-pyrenyl)phenyl)pyrene (PPP), 1-(2,5-dimethoxy-4-(1-pyrenyl)-phenyl)pyrene (DOPPP), 1-(2,5-dimethyl-4-(1-pyrenyl)phenyl) pyrene (DMPPP), 4,4'-N,N'-dicarbazole-biphenyl (CBP), 1,3-bis (9-carbazolyl)benzene (mCP), or p-bis(triphenylsilyly)benzene (UGH2), or a guest emitter, e.g. Bis(3,5-Difluoro-2-(2-pyridyl)phenyl-(2-carboxypyridyl)iridium(III) (FIrPic), Tris(2-phenylpyridine)iridium(III) Ir(PPy)$_3$, or 4,4'-bis[2-14-(N,N-diphenylamino)phenyl}vinyl]biphenyl. (DPAVBi).

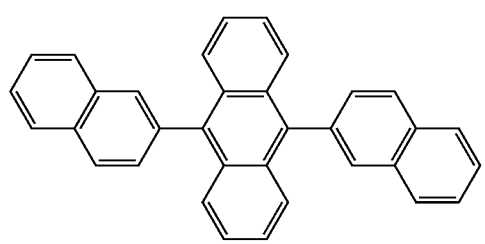

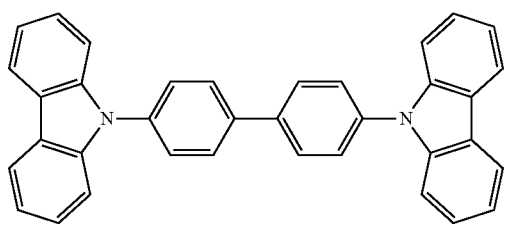

-continued
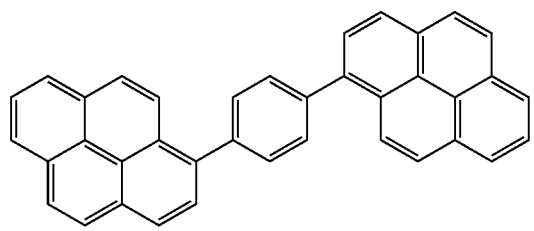
PPP
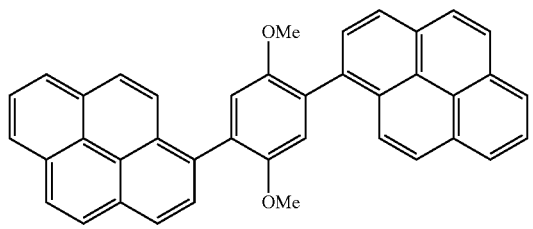
DOPPP
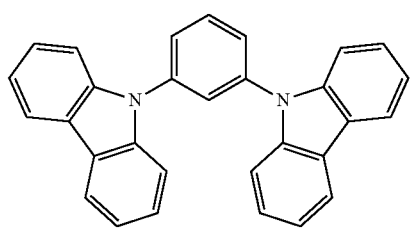
mCP
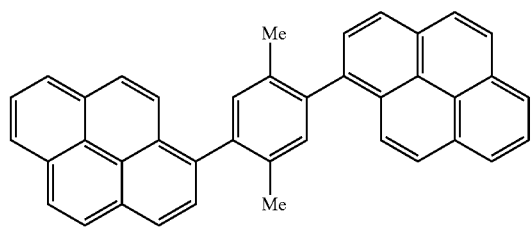
DMPPP
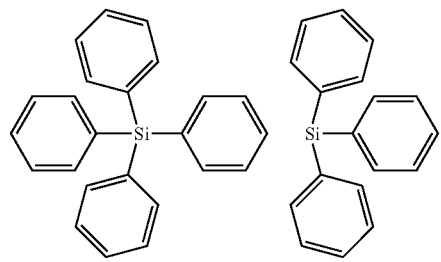
UGH2
Guest emitter
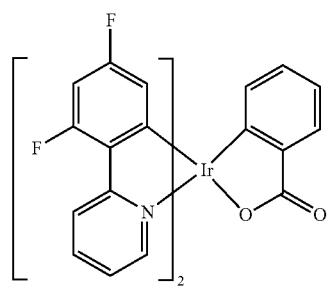
Irppy

Irppy

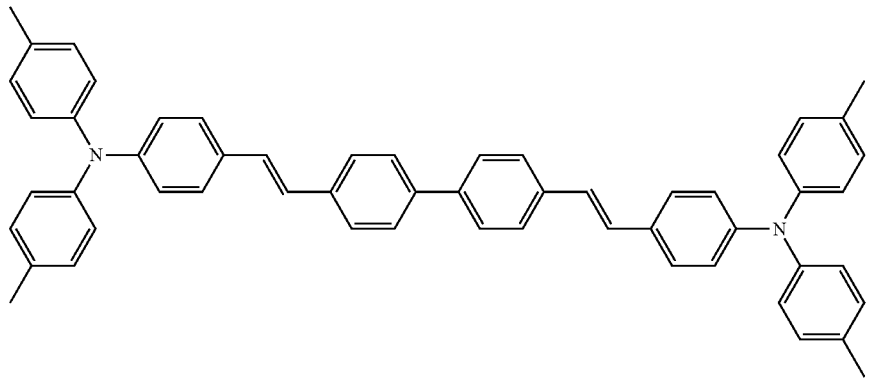

DPAVBi

Examples for EL device preparation are herein disclosed. An EL device may be fabricated by vacuum deposition of the materials at <5×10⁻⁶ Torr onto a clean glass precoated with a layer of indium tin oxide (ITO) with a sheet resistance of 25 ohm/square. The deposition rate for organic compounds is 1-2 Ås⁻¹. The cathode may be made by deposition of LiF (1.0 nm) and then Al (100 nm) with deposition rates of 0.1 and 2-3 Ås⁻¹, respectively. The effective area of the emitting diode is 9.00 mm².

The observed intense blue emission and high $T_g$ for the bis-phenanthroimidazolyl derivatives suggest their suitability to serve as blue host emitters in OLED applications. Blue-emitting EL devices include a device configuration of ITO/HTL (hole-transporting layer) (50 nm)/PPIP (30 nm)/BCP (2,9-dimethyl-4,7-diphenyl-1,10-phenanthroline) (15 nm)/Alq₃ (tris(8-hydroxyquinolinato)aluminum) (50 nm)/LiF (1 nm)/Al (100 nm). Here three different HTLs are utilized, including NPB (4,4'-bis[N-(1-naphthyl)-N-phenylamino]biphenyl), TPD (N,N'-di-m-tolyl-N,N'-diphenyl-1,1'-biphenyl-4,4'-diamine), TCTA (4,4',4''-tris(N-carbazolyl)triphenyl amine), to probe the EL properties of bis-phenanthroimidazolyl compounds. PPIP is selected as one of the preferred host emitters for further evaluation because of its higher PL (photoluminescence) efficiency.

Figure 3:
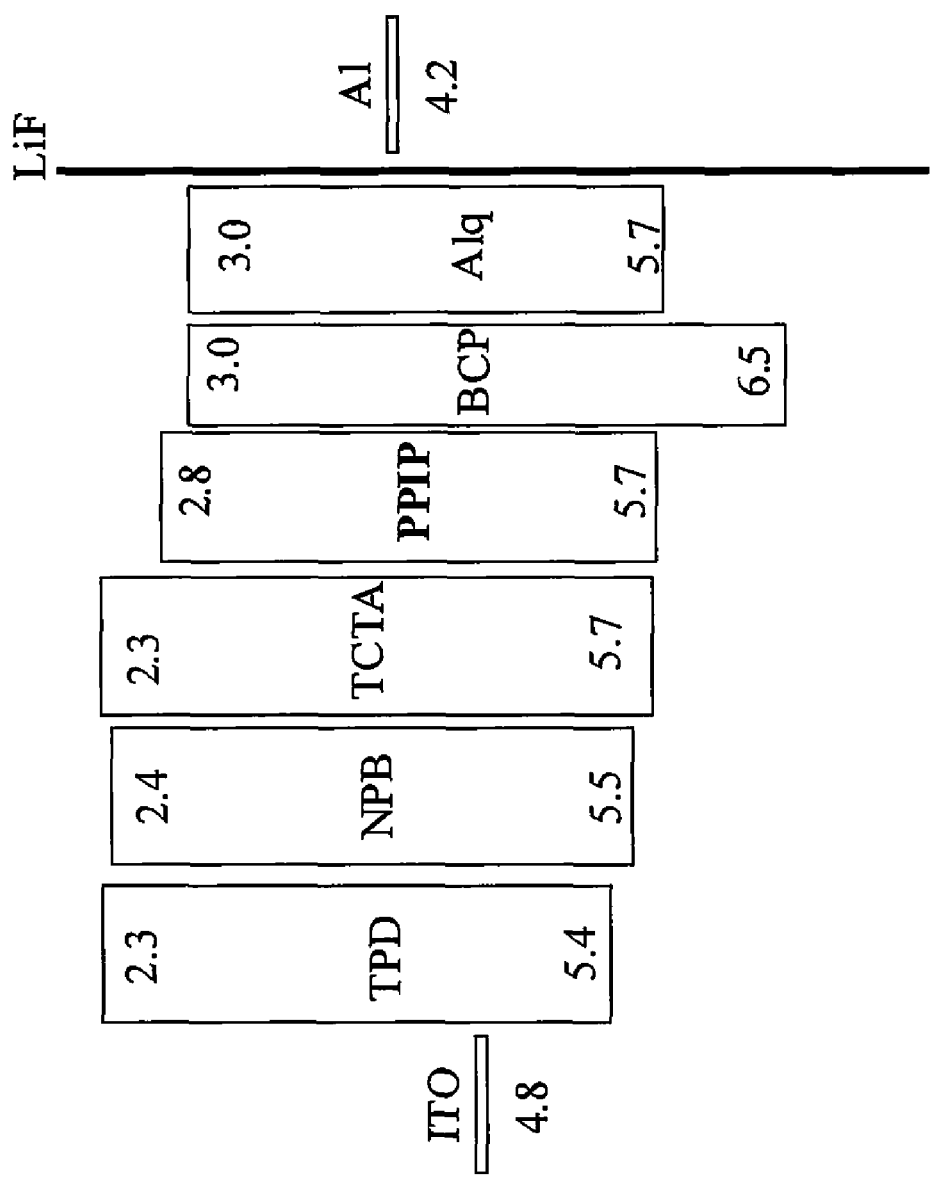
FIG. 3 is a schematic diagram illustrating the energy level and chemical structures of the material used in a blue light electroluminescent device according to an embodiment of the present invention.
Figure 4:
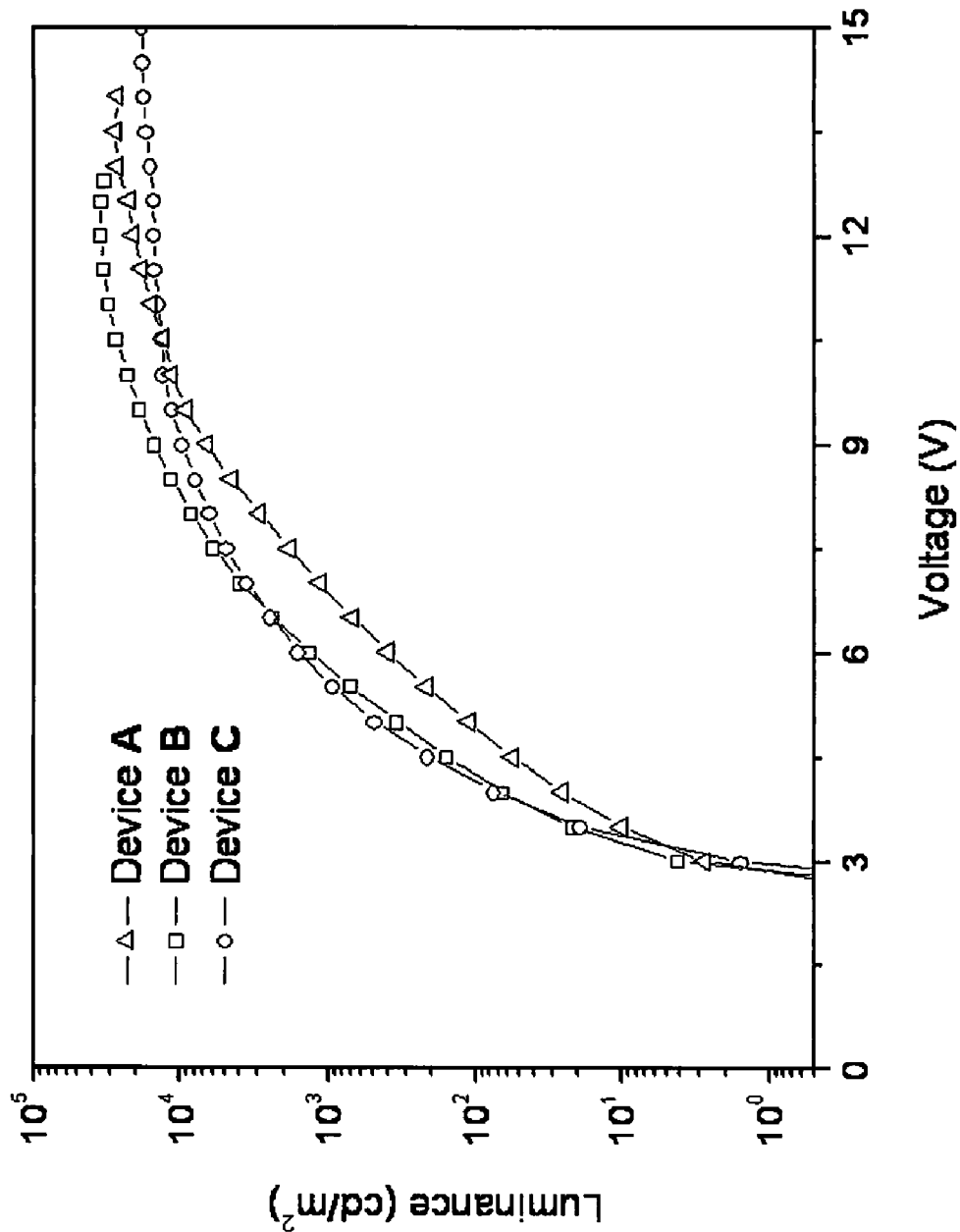
FIG. 4 to FIG. 7 are diagrams illustrating the experimental outcomes according to an embodiment of the present invention.
Figure 5:
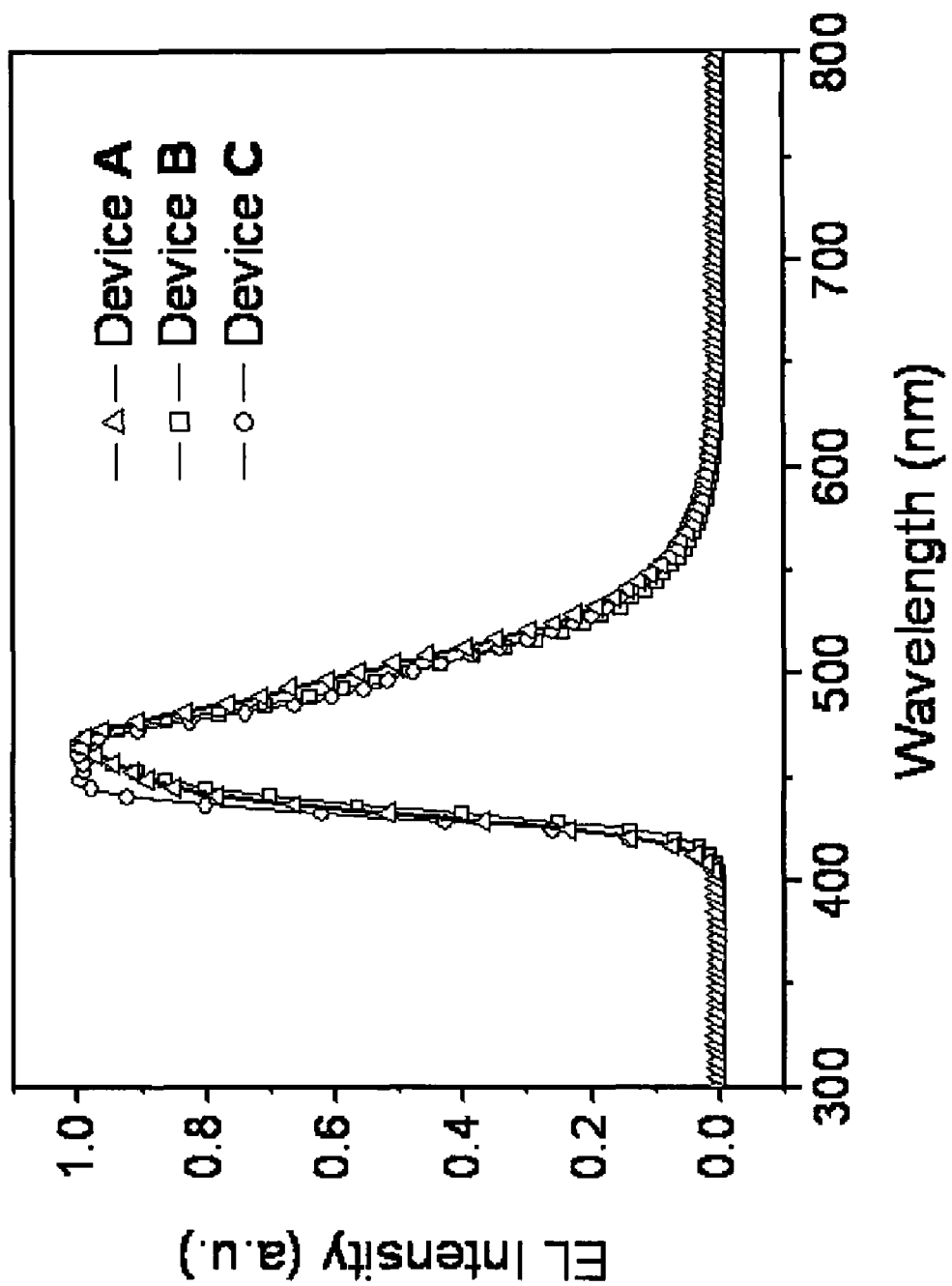
Figure 6:
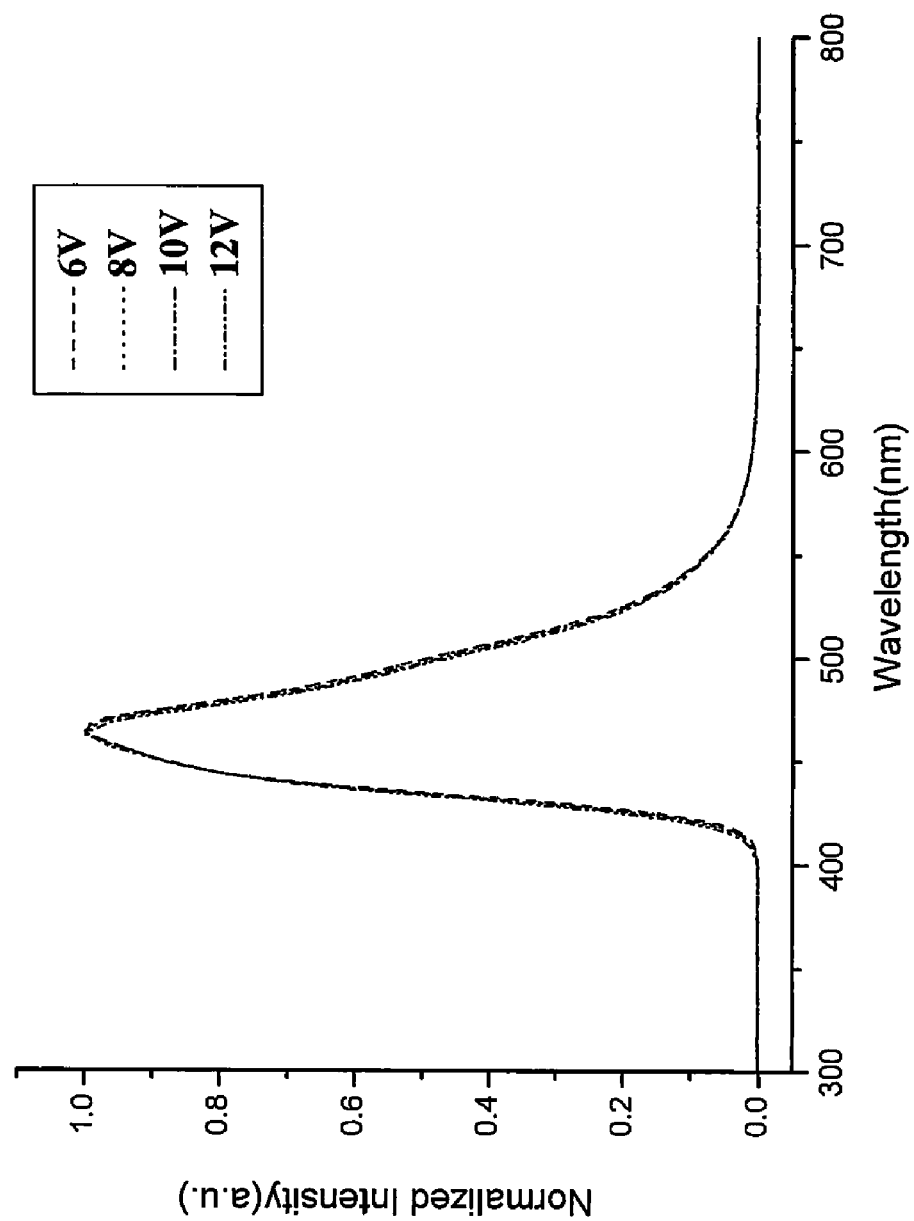

The device structures and the resulting performances are illustrated in Table 2, and the energy levels and the chemical structures of the materials are illustrated in FIG. 3. It is clear from FIG. 4 that the three bis-phenanthroimidazolyl compound-based devices are turned on at a relatively low voltage of <~4 V and then reach the maximum brightness at 12~15 V. The resulting EL spectra are illustrated in FIG. 5 and similar to the above-mentioned PL spectrum of PPIP in solid state. All the three devices emitted pure-blue light with $CIE_y \leq 0.15$ and these values are close to that of the blue standard for a video display recommended by the National Television Standards Committee (NTSC). Additionally, these bis-phenanthroimidazolyl compound-based devices also exhibited stable EL spectra at a wide range of applied voltages. Taking device B for example, the EL spectra were unchanged as voltages increased from 6 V to the voltage required for the maximum brightness (FIG. 6).

TABLE 2

Performance of bis-phenanthroimidazolyl compound-based OLEDs[a]

| Device (HTL)[b] | $V_{on}$ (V)[c] | L (cd/m², V) | $\eta_{ext}$ (%) | $\eta_c$ (cd/A) | $\eta_p$ (1 m/W) | $\lambda_{max}$ (nm) | CIE (x, y) @8 V |
|---|---|---|---|---|---|---|---|
| A (TPD/PPIP) | 2.8 | 27680 (13.5) | 4.77 | 5.92 | 4.69 | 466 | (0.14, 0.15) |
| B (NPB/PPIP) | 2.9 | 34768 (12.0) | 5.41 | 6.45 | 5.13 | 464 | (0.14, 0.14) |
| C (TCTA/PPIP) | 3.0 | 18240 (15.0) | 6.31 | 7.47 | 7.30 | 462 | (0.15, 0.14) |
| D (TCTA/TPIP) | 3.9 | 17300 (14.0) | 5.43 | 4.69 | 2.71 | 445 | (0.15, 0.09) |
| E (TCTA/APIP) | 4.1 | 19680 (16.0) | 5.26 | 6.40 | 3.84 | 464 | (0.15, 0.15) |

[a]The brightness (L), external quantum efficiency ($\eta_{ext}$), current efficiency ($\eta_c$), and power efficiency ($\eta_p$) are the maximum values of the EL devices.
[b]Device configuration: ITO/HTL (50 nm)/(PPIP, TPIP, or APIP) (30 nm)/BCP (15 nm)/Alq (30 nm)/LiF (1 nm)/Al (100 nm)
[c]$V_{on}$ is defined as the voltage required for 1 cd/m².

In order to better understand the EL properties of the bis-phenanthroimidazolyl compound-based devices, the present invention determines the HOMO (highest occupied molecular orbital) and LUMO (lowest occupied molecular orbital) energy levels from the ultraviolet photoelectron spectrum and the optical band gap (calculated from the lowest-energy absorption edge of the UV-vis absorption spectrum). The HOMO/LUMO energy levels of PPIP are 2.8/5.7 eV. This host emitter possesses a low-lying LUMO level similar to that of a typical imidazole-based electron-transporting material TPBI (1,3,5-tris(N-phenylbenzimidizol-2-yl)benzene). According to the energy level diagram shown in the inset of FIG. 3, electrons could smoothly travel into PPIP layer by conquering small injection barriers of 0.2 eV from BCP layer which serves as electron-transporting and hole-blocking layers. On the other hand, the hole injection barriers between PPIP and the three different HTLs are also relatively small (<0.3 eV). Such small injection barriers for charge carriers may account for the observed relatively low turn-on voltages.

Figure 7:
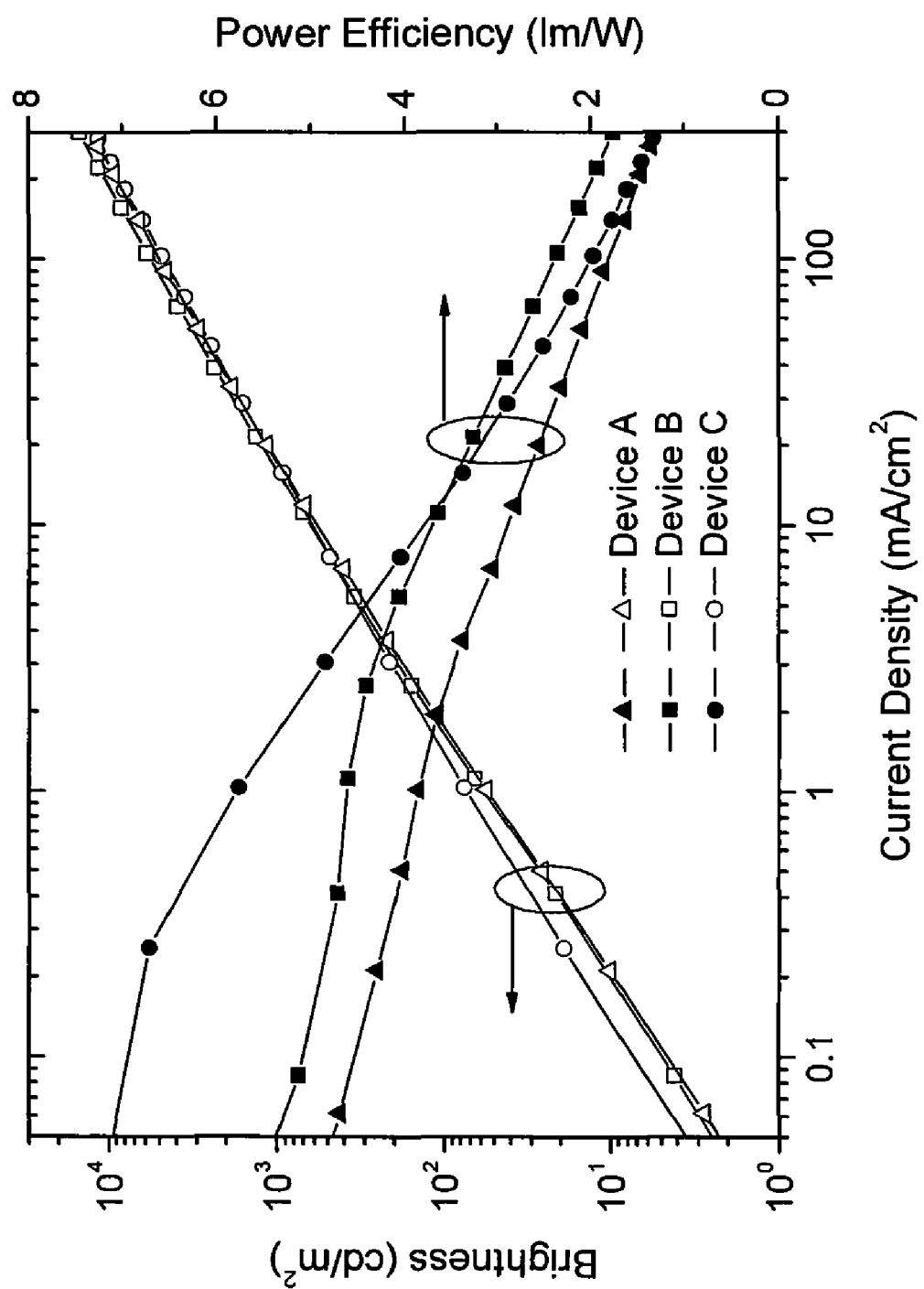

As shown in Table 2 and FIG. 7, the bis-phenanthroimidazolyl compound-based devices exhibited relatively high EL efficiency. The maximum external quantum efficiency and current efficiency achieved by these devices are 4.77~6.31% and 5.92~7.47 cd/A, respectively. When using TCTA as the HTL, the resulting device C can achieve the most efficient pure-blue light among the devices. This result could be attributed due to more balanced charge-transporting properties within the emissive layer achieved by better charge injection and confinement provided by TCTA HTL. Except for realizing the high $\eta_{ext}$ and $\eta_c$ values, the PPIP-based devices also preserve a relatively high level of power efficiency at 4.69~7.30 lm/W because of their low driving voltages. Although efficient non-doped OLEDs with extremely high external quantum efficiencies and excellent color purity have been reported, the corresponding peak power efficiencies are still relatively low (<4.5 lm/W). At a more practical brightness of 200 cd/m², the power efficiency of device C can still retain at a high level of ca. 5 lm/W (FIG. 7). It is noteworthy that device C would be the first reported OLED that emits pure-blue light with high power efficiency even at practical brightness levels.

To sum up, the present invention provides a compound for electron-transporting and electroluminescence. These materials exhibit excellent thermal properties with higher glass-transition temperature at around 200° C. and efficient blue emission at ca. 465 nm.

The present invention also provides an EL device giving relatively low turn-on voltages (<3 V) and pure-blue light with good color purity ($CIE_y \leq 0.15$). The preferred device realizes higher power efficiency of 7.30 lm/W. Moreover, the efficiency can still retain at a high level (5 lm/W) even as the brightness level increased up to 200 cd/m².

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A bis-phenanthroimidazolyl compound comprising the following formula:

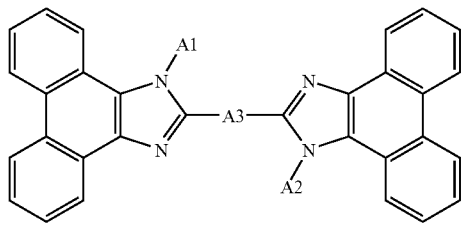

wherein A1 and A2 comprise identical or different aromatic rings, A3 is a member selected from the group consisted of naphthalene, anthracene, phenanthrene, chrysene, and pyrene, and each carbon in A1 to A3 and phenanthrol groups is independently substituted or non-substituted.

2. The bis-phenanthroimidazolyl compound as claimed in claim 1, wherein at least one of the carbons in A1 to A3 and phenanthrol groups is substituted, and a substituent group of substituted carbons in A1 to A3 and phenanthrol groups is a member selected from the group consisting of a halogen atom, a C1~C20 alkyl chain, a C1~C20 alkoxyl chain, a C1~C20 halogen substituted alkyl chain, a C1~C20 halogen substituted alkoxyl chain, a carbonyl group, a cyano group and a nitro group.

3. The bis-phenanthroimidazolyl compound as claimed in claim 1, wherein the A1 is a member selected from the group consisting of non-, methyl-, and methoxyl-substituted phenyl ring.

4. The bis-phenanthroimidazolyl compound as claimed in claim 1, wherein the A2 is a member selected from the group consisting of non-, methyl-, and methoxyl-substituted phenyl ring.

5. An electroluminescent device, comprising:
a cathode;
an anode; and
an organic layer provided in between the cathode and the anode, wherein the organic layer comprises a bis-phenanthroimidazolyl compound comprising the following formula:

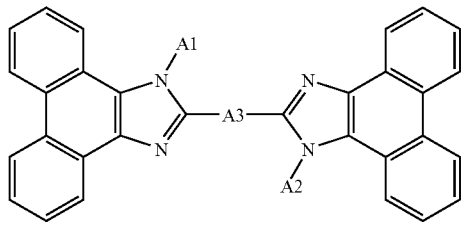

where A1 and A2 comprise identical or different aromatic rings, A3 is a member selected from the group consisted of naphthalene, anthracene, phenanthrene, chrysene, and pyrene, and each carbon in A1 to A3 and phenanthrol groups is independently substituted or non-substituted.

6. The electroluminescent device as claimed in claim 5, wherein wherein at least one of the carbons in A1 to A3 and phenanthrol groups is substituted, and a substituent group of substituted carbons in A1 to A3 and phenanthrol groups is a member selected from the group consisting of a halogen atom, a C1~C20 alkyl chain, a C1~C20 alkoxyl chain, a C1~C20 halogen substituted alkyl chain, a C1~C20 halogen substituted alkoxyl chain, a carbonyl group, a cyano group and a nitro group.

7. The electroluminescent device as claimed in claim 5, wherein the A1 is a member selected from the group consisting of non-, methyl-, and methoxyl-substituted phenyl ring.

8. The electroluminescent device as claimed in claim 5, wherein the A2 is a member selected from the group consisting of non-, methyl-, and methoxyl-substituted phenyl ring.

9. The electroluminescent device as claimed in claim 5 further comprises a hole-transporting layer.

10. The electroluminescent device as claimed in claim 9, wherein the hole-transporting layer comprises a 4,4'-bis[N-(1-naphthyl)-N-phenylamino]biphenyl (NPB), N,N'-di-m-tolyl-N,N'-diphenyl-1,1'-biphenyl-4,4'-diamine (TPD), or 4,4',4''-tris(N-carbazolyl)triphenyl amine (TCTA).

11. The electroluminescent device as claimed in claim 9 further comprises an electron-transporting layer.

12. The electroluminescent device as claimed in claim 11, wherein the electron-transporting layer comprises a metal chelate, 1,3,4-oxadiazole or 1,2,4-triazole or a derivative thereof, a thiopyran sulfone or a derivative thereof, or bis(benzimidazolyl)perylenedicarboximide.

13. The electroluminescent device as claimed in claim 5 further comprising an emitter layer.

14. The electroluminescent device as claimed in claim 13, wherein the emitter layer comprises a host emitter or a guest emitter.

15. The electroluminescent device as claimed in claim 14, wherein the host emitter comprises 9,10-Di(naphth-2-yl)anthracene (ADN), 1-(4-(1-pyrenyl)phenyl)pyrene (PPP), 1-(2,5-dimethoxy-4-(1-pyrenyl)-phenyl)pyrene (DOPPP), 1-(2,5-dimethyl-4-(1-pyrenyl)phenyl)pyrene (DMPPP), 4,4'-N,N'-dicarbazole-biphenyl (CBP), 1,3-bis (9-carbazolyl) benzene (mCP), or p-bis(triphenylsilyly)benzene (UGH2).

16. The electroluminescent device as claimed in claim 14, wherein the guest emitter comprises Bis(3,5-Difluoro-2-(2-pyridyl)phenyl-(2-carboxypyridyl)iridium(III) (FIrPic), Tris (2-phenylpyridine)iridium(III), (IrPPy)$_3$, or 4,4'-bis[2-14-(N,N-diphenylamino)phenyl}vinyl] biphenyl (DPAVBi).

* * * * *